United States Patent
Burdess et al.

(10) Patent No.: US 6,805,009 B2
(45) Date of Patent: Oct. 19, 2004

(54) RESONANT SENSOR

(75) Inventors: James Stonehouse Burdess, Whitley Bay (GB); Calum Jack McNeil, Newcastle Upon Tyne (GB)

(73) Assignee: Newcastle University Ventures LTD, Tyne & Wear (GB)

(*) Notice: Subject to any disclaimer, the term of this patent is extended or adjusted under 35 U.S.C. 154(b) by 0 days.

(21) Appl. No.: 10/470,340

(22) PCT Filed: Jan. 21, 2002

(86) PCT No.: PCT/GB02/00237
§ 371 (c)(1),
(2), (4) Date: Jul. 28, 2003

(87) PCT Pub. No.: WO02/063264
PCT Pub. Date: Aug. 15, 2002

(65) Prior Publication Data
US 2004/0051539 A1 Mar. 18, 2004

(30) Foreign Application Priority Data
Feb. 5, 2001 (GB) .............................. 0102832

(51) Int. Cl.$^7$ .............................................. G01H 13/00
(52) U.S. Cl. .............................. 73/579; 73/580; 422/69
(58) Field of Search ........................ 73/580, 579, 24.06, 73/61.49, 61.75, 61.79; 422/69

(56) References Cited

U.S. PATENT DOCUMENTS

| | | | |
|---|---|---|---|
| 4,144,747 A | * | 3/1979 | Datwyler, Jr. ............ 73/862.59 |
| 4,399,686 A | | 8/1983 | Kindlund et al. |
| 5,455,475 A | | 10/1995 | Josse et al. |
| 5,705,399 A | | 1/1998 | Larue |
| 5,852,229 A | | 12/1998 | Josse et al. |

\* cited by examiner

*Primary Examiner*—John E. Chapman
(74) *Attorney, Agent, or Firm*—Stites & Harbison PLLC; Douglas E. Jackson

(57) ABSTRACT

A resonant sensor for determining structural property changes, in particular for detecting the presence of chemical or biological species, comprises a structure (2) mounted to be capable of resonating and having a cyclically symmetrical configuration with two independent degenerative modes of vibration of a common natural frequency (f), and means (24,26,28,30,32,34,36,38) for exciting the structure (2) to resonate according to the two degenerative modes, regions (8,12,16,20) of the structure (2) being modified such that, on changes in the structural properties of the modified regions (8,12,16,20), for example by the addition or subtraction of mass, the natural frequencies (f1, f2) of the two modes of vibration become different, the difference in frequencies (?f) being proportional to the change in structural properties.

7 Claims, 3 Drawing Sheets

RESONANT SENSOR

TECHNICAL FIELD

The present invention relates to resonant sensors for determining structural property changes, and has particular though not exclusive application to such sensors for detecting the presence of chemical or biochemical species.

BACKGROUND TO THE INVENTION

It is well established practice to provide resonant mass sensors in which the change in resonant frequency which occurs on the application of mass to the sensor is used to calculate the value of the applied mass.

However, such devices rely upon absolute changes in frequency to determine the added mass, the devices commonly operating at frequencies of the order of 10–100 $MH_z$. As changes of less than 1000 $H_z$ often need to be measured, the stability of the oscillator is of great importance, precise thermal characteristics and other associated parameters of the environment needing to be known to achieve meaningful mass measurements.

SUMMARY OF THE INVENTION

It would be desirable to be able to provide a resonant sensor more readily and directly able than heretofore to measure structural property changes, such as the addition of mass to, or the subtraction of mass from, the sensor, the measurements being independent of environmental conditions.

According to the present invention there is provided a resonant sensor for determining structural property changes, the sensor comprising a structure mounted to be capable of resonating, the structure having a cyclically symmetrical configuration with two independent degenerate modes of vibration of a common natural frequency, and means for exciting the structure to resonate according to said two degenerate modes, regions of the structure being modified such that, on changes in the structural properties of the modified regions, the natural frequencies of the two modes of vibration become different, the difference in frequencies being proportional to the change in structural properties.

Thus it will be appreciated that when, for example, a chemical or biological species is incident upon the modified regions of the surface to change the mass of said regions, the cyclic symmetry of the sensor is destroyed, and a frequency split of the previously degenerate modes is created. The value of the difference in frequencies enables the added mass to be calculated.

As any frequency change in the two modes caused by, for example, variations in temperature, pressure and internal stress in the structure are the same in each mode, these factors do not contribute to the value of the frequency split, and need not be known to determine the desired property change—the arrangement is thus self-compensating for these external effects, and requires only a single readout of the frequency difference to be made to enable calculation of the structural change under question.

The resonant structure may comprise a diaphragm, the periphery of which may be secured to a supporting substrate, the modified regions of the diaphragm being on the upper surface thereof, the means for exciting the diaphragm being located below the diaphragm symmetrically disposed relative to said modified regions, which means may be, for example, electrostatic, magnetic, piezoelectric or the like.

The modified regions of the diaphragm may be of, for example, gold chemically treated to promote bonding with specified chemical or biological species the presence of which is to be detected.

DESCRIPTION OF THE PREFERRED EMBODIMENTS

The present invention is based upon cyclically symmetrical structures with pairs of independent modes of vibration that share a common natural frequency of vibration.

The theory behind such structures will now be detailed with reference to FIGS. 1 to 3 of the accompanying drawings.

A cyclically symmetric structure is formed from segments, which are derived from a base segment by successive rotations through a defined angle about a fixed axis. If the base segment spans an angle of 360°/n, where n must be an integer in order to form a connected structure, then the resulting structure formed from the rotations has a rotational symmetry of order n.

Figure 1:
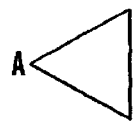
FIG. 1 illustrates a base segment of a structure in the form of a diaphragm of a sensor according to the invention.
Figure 2:
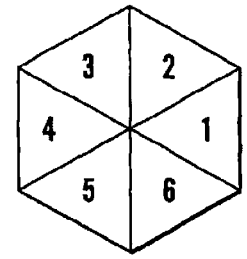
FIG. 2 illustrates a diaphragm of a sensor according to the invention.

For example, consider the equilateral triangle shown in FIG. 1 and let this be the base segment. If a structure is formed from this triangle by successive rotations of 60° about an axis which is normal to the plane of the paper and which passes through the apex at A, then a hexagon is formed, as shown in FIG. 2. This resulting structure has a cyclical symmetry of order 6.

It is known that cyclically symmetric structures have pairs of independent modes of vibration that share a common natural frequency of vibration. This feature is called modal degeneracy. When vibrating at a natural frequency f, the displaced shape u of the complete structure can always be considered as a vector formed from the displacements of each segment—ie. $u=(u_1,u_2, \ldots u_n)$. In the case of the hexagon, n=6. If the modal displacements are such that u does not satisfy $u=u_1(1, 1, \ldots 1)$ and $u=u_1(1, -1, 1, -1 \ldots 1, -1)$ then the mode is degenerate. If $u=(u_1,u_2, \ldots u_n)$ is one of the degenerate modes then $u=(u_n,u_1,u_2, \ldots ,u_{n-1})$, obtained by rotating the displaced shape through one segment, is the other mode.

Figure 3A:
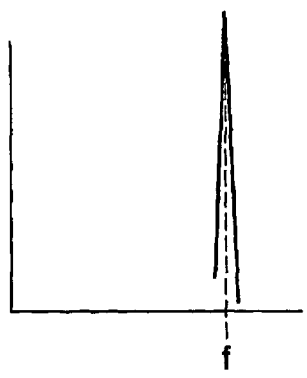
FIGS. 3a and 3b show, respectively, the common resonant frequency of the two independent modes of vibration of a cyclically symmetric structure, and the frequency split of said modes on modification of the cyclic symmetry.
Figure 3B:
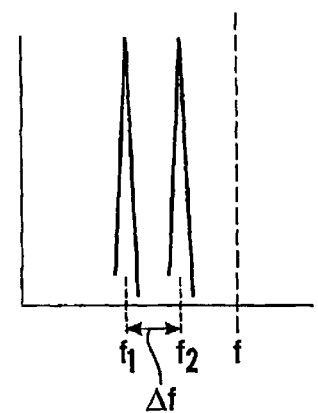

If this symmetry is disrupted, for example by the addition or removal of mass, then the natural frequencies associated with the once degenerate modes become unique to each mode, changing from f to $f_1$ and from f to $f_2$ as shown in FIG. 3, such that a frequency split of value $\Delta f$ exists between the two modes. This split in frequency can be used as a measure of the 'breakage' in the cyclic symmetry, and, in the case of a mass sensor, is a function of the change in mass.

Figure 4:
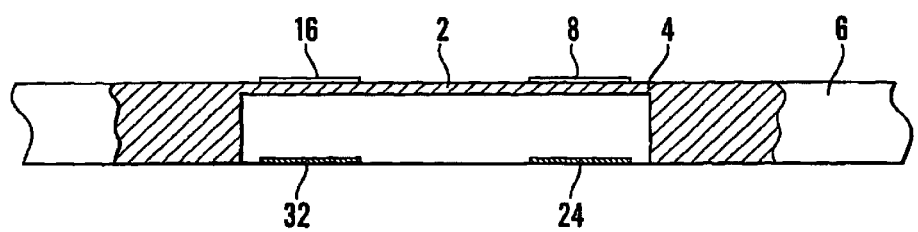
FIG. 4 is a transverse section through part of a first sensor according to the invention.
Figure 5:
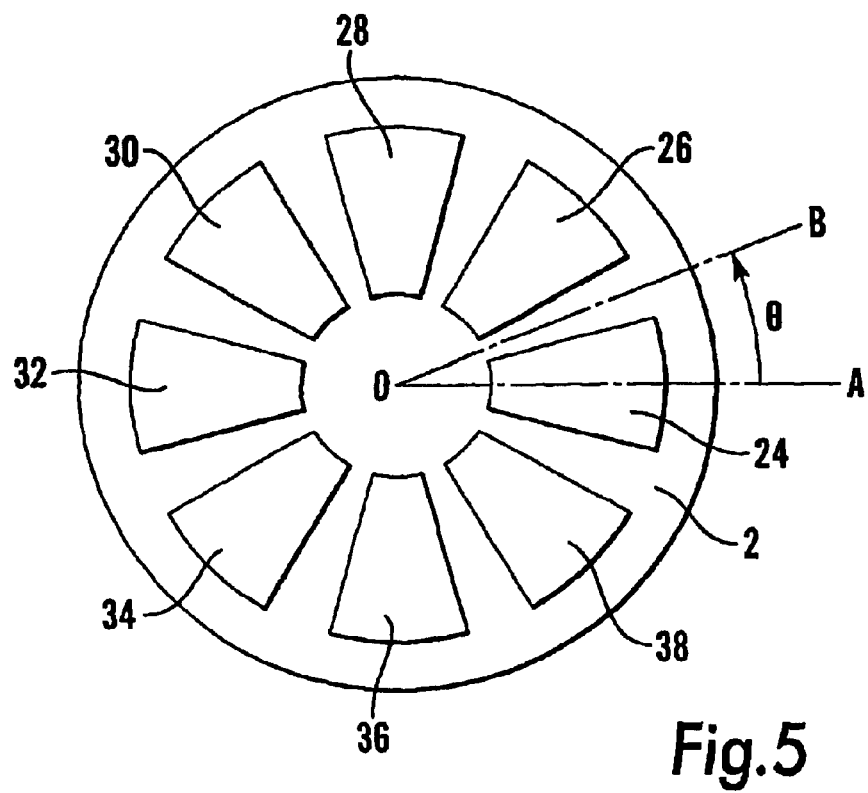
FIG. 5 is a plan view from below of the diaphragm of the sensor of FIG. 4.
Figure 6:
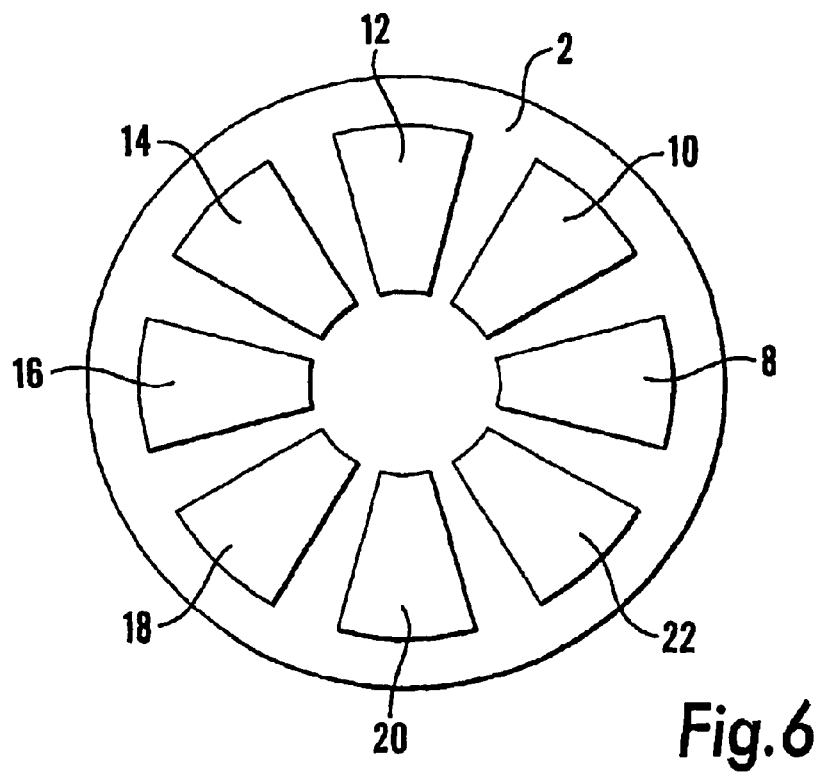
FIG. 6 is a plan view from above of the diaphragm of the sensor of FIG. 4.

A practical application of this concept is illustrated in FIGS. 4 to 6. in these drawings there is shown a structure in the form of a circular diaphragm 2 of relatively thin electrically conductive material the periphery of which is fixed at 4 to a thicker supporting substrate 6.

Deposited on the upper surface of the diaphragm 2 are eight equi-spaced regions 8,10,12,14,16,18,20,22, for example of gold, whereby the diaphragm 2 has a cyclic symmetry of the order eight.

The material of the regions 8 to 22 is chosen such that it can be chemically treated to promote bonding with a specified chemical or biological species to be monitored. In the case of a mass sensor, the regions 8,12,16 and 20 are modified, while regions 10,14,18 and 22 remain unmodified.

Positioned immediately below the lower surface of the diaphragm 2 are eight actuating and sensing electrodes 24,26,28,30,32,34,36,38, one associated with each of the regions 8 to 22.

Electrodes 24,28,32 and 36 are used to produce a resonant flexural response in the diaphragm 2 by electrostatic means, and the subsequent modal motion of the diaphragm can be made to be of the form which varies circumferentially as cos 2θ, for a structure with eight fold symmetry (see FIG. 5). The angle θ defines a line OB in the plane of the diaphragm measured from a datum line OA which is chosen to bisect the region 8. In this case all points on the line OB have a displacement proportional to cos 2θ.

In a similar manner, electrodes 26,30,34 and 38 when actuated excite a resonant flexural response in the diaphragm the modal motion of which varies circumferentially as sin 2θ.

These modal motions are degenerate, and thus share a common natural frequency.

When a chemical or biological species is deposited on the modified regions 8,12,16 and 20, the mass of these regions changes, and the cyclic symmetry of the diaphragm 2 is broken.

As detailed above, a measurement of the frequency split of the once degenerate modes enables the mass added to the modified regions to be calculated. Frequency changes caused by changes in temperature, pressure and internal stress in the diaphragm 2 are the same in each mode, and thus do not contribute to the value of the frequency split, the arrangement therefore being self-compensating for these effects.

Modifications and variations from the sensor described and illustrated can be made without departing from the scope of the appended claims. In particular, the sensor can be used to determine a variety of structural property changes, including reduction in mass, the electrodes 24 to 38 may be replaced by other exciting means which may be, for example electrostatic, magnetic or piezoelectric in operation, the regions 8 to 22 may be of any suitable material other than gold, and the cyclic symmetry of the diaphragm may be other than eight, as may the number of regions 8 to 22 and exciting means 24 to 38.

Figure 7:
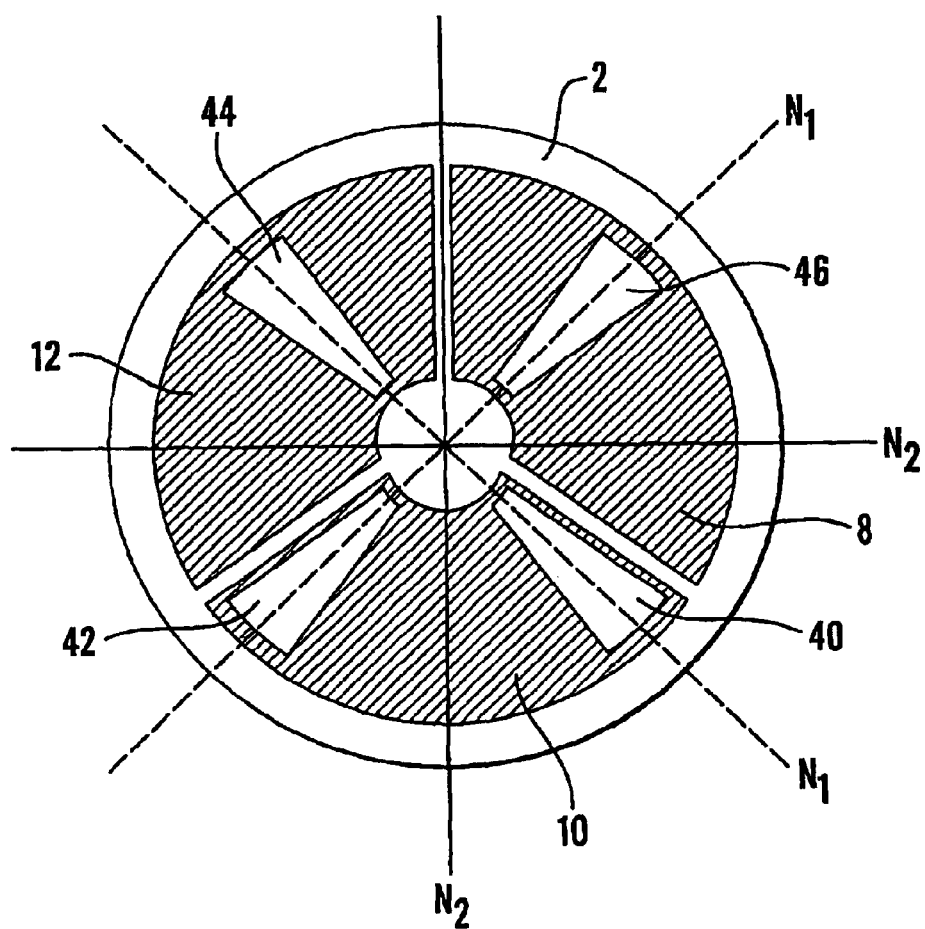
FIG. 7 is a plan view from above of a diaphragm of a further sensor according to the invention.

Referring to FIG. 7, there is shown a diaphragm 2 designed to have a three fold cyclic symmetry. The symmetry can be achieved by having three identical equi-spaced 'electroded' regions 8,10,12 deposited on the upper surface of the diaphragm 2. This diaphragm 2 still has degenerate modes of the form cos 2θ and sin 2θ with two identical natural frequencies.

The mode characterised by cos 2θ has the nodal lines shown by dotted lines $N_1$, while the mode characterised by sin 2θ has nodal lines shown by full lines $N_2$.

The regions 8,10,12 are chemically treated to form four sub-regions 40,42,44 and 46 thereon symmetrically disposed either side of the nodal lines $N_1$, these sub-regions being such as to allow a chemical or biological species to bind to the surface of the diaphragm 2 thereby to change the mass of the diaphragm 2 in the sub-regions 40 to 46.

Because the added mass is disposed equally about the nodal lines of the cos 2θ mode, its effect on the natural frequency of this mode is small. The same is not however the case for the sin 2θ mode the frequency of which is changed to a greater degree, with the result that a split in the natural frequencies of the once degenerate modes occurs.

Other modifications and variations will be apparent to those skilled in the art.

What is claimed is:

1. A resonant sensor for determining structural property changes characterised by a structure (2) mounted to be capable of resonating, the structure (2) having a cyclically symmetrical configuration with two independent degenerative modes of vibration of a common natural frequency, and means (24,26,28,30,32,34,36,38) for exciting the structure (2) to resonate according to said two degenerate modes, regions (8,12,16,20) of the structure (2) being modified such that, on changes in the structural properties of the modified regions (8,12,16,20), the natural frequencies ($f_1,f_2$) of the two modes of vibration become different, the difference in frequencies (Δf) being proportional to the change in structural properties.

2. A sensor as claimed in claim 1 in which the structure comprises a diaphragm (2) the periphery of which is secured to a supporting substrate (6), the modified regions (8,12,16, 20) of the diaphragm (2) being on the upper surface thereof, the means (24,26,28,30,32,34,36,38) for exciting the diaphragm (2) being located below the diaphragm (2) symmetrically disposed relative to said modified regions (8,12, 16,20) of the diaphragm.

3. A sensor as claimed in claim 2 in which the means (24,26,28,30,32,34,36,38) for exciting the diaphragm (2) are electrostatic, magnetic or piezoelectric in operation.

4. A sensor as claimed in claim 2 or claim 3 in which the diaphragm (2) is of electrically conductive material, the means (24,26,28,30,32,34,36,38) for exciting the diaphragm (2) comprising electrodes.

5. A sensor as claimed in any one of claims 2 to 4 in which there are a plurality of regions (8,10,12,14,16,18,20,22) defined on the upper surface of the diaphragm (2) equispaced therearound, alternate regions (8,12,16,20) being modified and the remaining regions (10,14,18,22) being unmodified, associated electrodes (24,28,32,36) being positioned below the modified regions (8,12,16,20) to produce a first resonant flexural response in the diaphragm (2) on excitation thereof, and associated electrodes (26,30,34,38) being positioned below the unmodified regions (10,14,18, 22) to produce a second resonant flexural response in the diaphragm (2) on excitation thereof.

6. A sensor as claimed in claim 1 in which alternate regions are modified by chemical treatment to promote bonding with a species to be monitored.

7. A sensor as claimed in claim 6 in which the regions are of gold.

* * * * *